(12) United States Patent
Thennati et al.

(10) Patent No.: US 6,380,436 B1
(45) Date of Patent: Apr. 30, 2002

(54) PROCESS FOR THE SYNTHESIS OF ALKOXYALKYL (TRIFLUORMETHYLPHENYL) METHANONES

(75) Inventors: Rajamannar Thennati; Keshav Deo; Ajay Sohanlal Midha; Tilak Chandra; Vijay Muljihhai Patel, all of Baroda (IN)

(73) Assignee: Sun Pharmaceutical Industries Ltd. (IN)

( * ) Notice: Subject to any disclaimer, the term of this patent is extended or adjusted under 35 U.S.C. 154(b) by 0 days.

(21) Appl. No.: 09/700,292

(22) PCT Filed: Mar. 30, 1999

(86) PCT No.: PCT/IN99/00010

§ 371 Date: Feb. 23, 2001

§ 102(e) Date: Feb. 23, 2001

(87) PCT Pub. No.: WO99/58485

PCT Pub. Date: Nov. 18, 1999

(30) Foreign Application Priority Data

May 12, 1998 (IN) ......................... 275/BOM/98

(51) Int. Cl.$^7$ ......................... C07C 45/44; C07C 45/46; C07C 49/76
(52) U.S. Cl. ......................... 568/309; 568/322; 568/336
(58) Field of Search ......................... 568/309, 322, 568/336

(56) References Cited

U.S. PATENT DOCUMENTS

| | | | |
|---|---|---|---|
| 3,732,307 A | 5/1973 | Middleton | 260/566 |
| 3,962,257 A | 6/1976 | Pioch et al. | 260/293.8 |
| 4,085,225 A | 4/1978 | Welle et al. | 424/304 |
| 4,536,518 A | 8/1985 | Welch, Jr. et al. | 514/647 |
| 4,556,676 A | 12/1985 | Welch, Jr. et al. | 514/554 |

FOREIGN PATENT DOCUMENTS

| | | |
|---|---|---|
| EP | 0004733 | 10/1979 |
| EP | 0007843 | 2/1980 |
| EP | 0028901 | 5/1981 |
| EP | 0030081 | 6/1981 |

OTHER PUBLICATIONS

Chastrette .M, et al. "Effect of Salts on Organometallic Reaction. Kinetic Study of the Organomagnesium–Benzonitrite Reaction" J. Organomed. Chem Abstract, vol. 78 (1974), 303–311.
Lalezari, I. et al. "Synthesis and Pharmacological Activity of Dialkylaminoalkyl Esters of Benzilic Acids . . . " Journal of Medicinal Chemistry, vol. 14, No. 11, p. 1138–1140, (1971).
Capillon, J. et al. "Reduction Asymetrique de Benzophenones Substituees" Abstract in English Tetrahedron, vol. 35, p. 1807–1815, (1979).
Filler, R. et al. "Fluorinated Aromatic Amino Acids. I. o–,m–, and p–Trifluoromethylphenylalanines" J. Organic Chemistry, vol. 25, p. 733, (1960).
Haller, H.L. et al. "The Action of Isobutylmagnesium Bromide on 3,4,5–Trimethoxybenzonitrile" J. Am. Chem. Soc. vol. 61, p. 2175–2177, (1939).
Richtzenhain, H. et al. "Substitulionsreaktionen mit Metallorganischen Verbindungen . . . " Berichte 77B, p. 566–572, (1944).
Schaefer, F.C. The Chemistry of the Cyano Group (1970) Ed. Z. Rappoport, Interscience Publishers, p. 276–303.
Gilman, H. et al. "The Relative Reactivities of Organolithium and Organomagnesium Compounds" J. Am. Chem. Soc. vol. 55, p. 1265–1569, (1933).
Swain, C.G. "The Mechanism of Addition of Grignard Reagents to Nitriles" J. Am. Chem. Soc. vol. 69, p. 2306, (1947).
Biemann, K. Spectral Data for Structural Determination of Organic Compounds, Springer–Verlag 1989 p. C245.

Primary Examiner—James O. Wilson
Assistant Examiner—Sikarl A. Witherspoon
(74) Attorney, Agent, or Firm—Ladas & Parry

(57) ABSTRACT

A new process is described for the preparation of (alkoxyalkyl)(4-trifluoromethylphenyl)methanones. The process comprises reacting a 4-trifluoromethylbenzonitrile with an alkoxyalkyl Grignard in the presence of a suitable polar aprotic solvent. The compound (4-methoxybutyl)(4-trifluoromethylphenyl)methanone is useful as an intermediate in the preparation of the antidepressant drug fluvoxamine.

32 Claims, No Drawings

PROCESS FOR THE SYNTHESIS OF ALKOXYALKYL (TRIFLUORMETHYLPHENYL) METHANONES

FIELD OF THE INVENTION

The present invention relates to a process for the preparation of (alkoxyalkyl)(4-trifluoromethylphenyl)methanones of formula I:

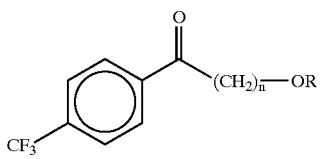

in which R is selected from a lower alkyl having 1 to 3 carbon atoms and n is an integer from 3 to 6.

BACKGROUND OF THE INVENTION

U.S. Pat. No. 4,085,225 claimed oxime ether compounds including fluvoxamine and also disclosed a process for their preparation. The process made use of an intermediate of formula I wherein n=4 and R is —$CH_3$. However, a process for the preparation of this intermediate was not disclosed.

U.S. Pat. Nos. 4,536,518 and 4,556,676 and EP 28,901 claimed tetrahydronaphthalenamine compounds, and disclosed a process for the preparation of the claimed compounds, in which process the starting materials were substituted benzophenones. The preparation of 4-trifluoromethylbenzophenone from 4-trifluoromethylbenzonitrile and phenylmagnesium bromide was exemplified. The present invention however is materially different in that it does not claim a process for the preparation of 4-trifluoromethylbenzophenones, but claims a process for the preparation of (alkoxyalkyl)(4-trifluoromethylphenyl)methanones (I). Moreover, the process reported in these prior art references was slow, requiring the reaction mixture to be stirred at room temperature for a period of 3 days giving 62% yield of 4-trifluoromethylbenzophenone.

U.S. Pat. No. 3,962,257 claimed phenacyl piperidines. Example 14 of the patent disclosed the preparation of 1-methyl-3-[3-(trifluoromethyl)phenacyl]piperidine from 3-trifluoromethylbenzonitrile and 1-methyl-3-piperidylmethylmagnesium chloride. The % yield obtained was not mentioned and the purification step disclosed in the example was relatively elaborate and time consuming. There was however no disclosure of the preparation of the compounds of formula I.

European Patent No. 7843 claimed propiophenone derivatives. Example I of the patent disclosed the preparation of 3-trifluoromethylpropiophenone from 3-trifluoromethylbenzonitrile and ethylmagnesium halide. However, there was no disclosure of a process for the preparation of compounds of formula I.

European Patent No. 4733 claimed diaryl substituted pyrazoline carboxanilides, intermediates for which were prepared from deoxybenzoin compounds. Example I

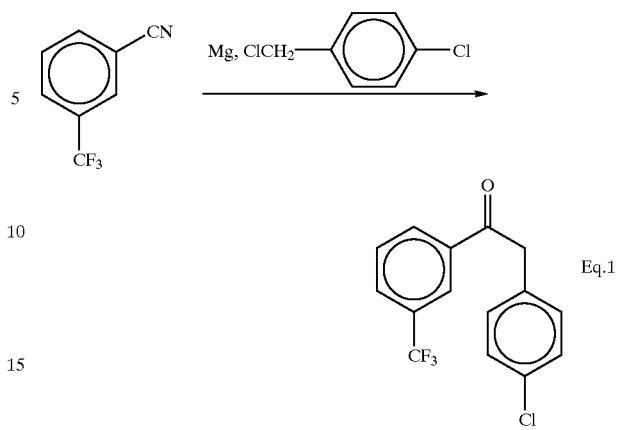

described the preparation of one such deoxybenzoin compound (as illustrated in Eq 1). However the example(s) disclosed a process using only 3-trifluoromethylbenzonitrile. The reaction conditions, yield and reaction time/rate for a process using 4-trifluoromethylbenzonitrile was not disclosed. This prior art did not disclose a process for the preparation of compounds of formula I.

The preparation of (benzyl)(3-trifluoromethylphenyl) methanone from 3-trifluoromethylbenzonitrile and benzylmagnesium chloride is disclosed in I. Larezari, M. Hatefi; Journal of Medicinal Chemistry, 14, 1138 (1971). This prior art did not disclose a process for the preparation of compounds of formula I.

The preparation of methoxy trifluoromethylacetophenone from 4-trifluoromethyl bromobenzene and methoxyacetonitrile in presence of Mg is disclosed in J. Capillon, J. P. Guette; Tetrahedron, 35, 1807 (1979). The product of this reaction is a compound of formula I where n is 1 and R is —$CH_3$. However, this prior art has no disclosure or suggestion, that a similar reaction could be used successfully to give high yields of the compounds of formula I where n is from 3 to 6. It was suspected that if a similar reaction were to be used for the preparation of compounds of the present invention the 4-trifluoromethylphenyl Grignard would be difficult to prepare. For example, it is reported that 4-trifluoromethylphenylmagnesium chloride is difficult to prepare even with many sets of reaction conditions (R. Filler, H. Novar; Journal of Organic Chemistry, 25, 733, (1960)). Also in the reaction of alkoxyalkylnitrile with 4-trifluoromethylphenyl Grignard it is possible that deprotonation from -methylene group of alkoxyalkylnitrile and subsequent formation of a nitrile anion could lead to condensation products. It is also well known to those skilled in the art that attempts to extend the result of the study of a particular Grignard reaction to other cases have frequently been disappointing. The solvent, substrate, reactant concentrations and temperature all appear to influence the nature of the reactive organomagnesium species. The complexity of even the normal addition reaction is such that small changes in reaction conditions may cause large effects on the output of the reaction. For example, 3,5-dimethoxybenzonitrile reacted with isobutylmagnesium bromide to form the corresponding ketone on hydrolysis (H. L. Haller, P. S. Schaffer; Journal of American Chemical Society, 61, 2175, (1939)), whereas 2,3-dimethoxybenzonitrile reacted with aliphatic Grignard reagents to form 2-alkyl-3-methoxybenzonitrile (H. Richtzenhain, P. Nippus; Berichte, 77B, 566, (1944)). Furthermore, investigations (The Chemistry of the Cyano Group, Ed. Z. Rappoport, Interscience Publishers, 1970, p. 277) of the reactivities of various substrates towards phenylmagnesium bromide have shown nitrites to be relatively unreactive (C. G. Swain; Journal of American Chemical Society, 69, 2306, (1947)). For example, p-dimethylaminobenzonitrile and p-methoxybenzonitrile failed to react with ethyl and phenylmagnesium bromide (H. Gilman, R. H. Kirby; Journal of American Chemical Society, 1265 (1933)).

In view of the above discussion describing the state of the art there was no known or apparently efficient and cost effective method for the preparation of compounds of formula I using Grignard reagents. Particularly, none of the above prior arts disclosed an alkoxyalkyl Grignard reagent or its reaction with a trifluoromethylbenzonitrile.

SUMMARY OF THE PRESENT INVENTION

The objective of the present invention is to develop a rapid and cost effective process for the preparation of (alkoxyalkyl)(4-trifluoromethylphenyl)methanones of formula I in high yields.

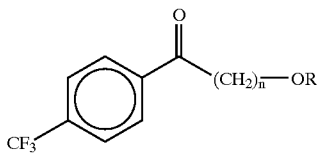

I

It has been surprisingly found that the process of the present invention, wherein a Grignard of alkoxyalkyl is reacted in a polar aprotic solvent with 4-trifluoromethylbenzonitrile, is a rapid and cost-effective process giving high yields of compounds of formula I. The reaction may be completed in about 1 hour to about 3 hours and can give yields of about 70%. Such a compound (where n=4 and R=CH$_3$) is useful as an intermediate in the preparation of fluvoxamine.

DESCRIPTION OF THE INVENTION

The present invention provides a process for the preparation of (alkoxyalkyl)(4-trifluoromethylphenyl)methanones of formula I:

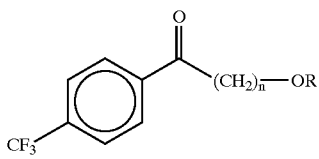

I wherein R is selected from a lower alkyl having 1 to 3 carbon atoms and n is an integer from 3 to 6. The (4-methoxybutyl)(4-trifluoromethylphenyl)methanone (II) is a crucial intermediate for the preparation of the antidepressant drug fluvoxamine.

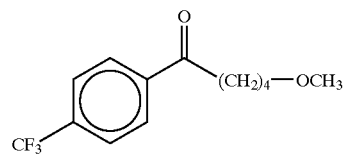

II

According to the process of the present invention (alkoxyalkyl)(4-trifluoromethylphenyl)methanones (I) are prepared by treating 4-trifluoromethylbenzonitrile (III), with an alkoxyalkyl Grignard (IV),

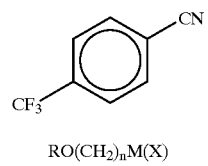

III

RO(CH$_2$)$_n$M(X)   IV wherein 'R' is selected from a lower alkyl having 1 to 3 carbon atoms, 'n' is an integer from 3 to 6, 'M' is magnesium and 'X' represents a halogen atom selected from Cl, Br or I.

In a preferred embodiment of the present invention 'X' is Br.

According to a preferred embodiment of the present invention the compound of formula I is (4-methoxybutyl)(4-trifluoromethylphenyl)methanone (II).

The alkoxyalkyl Grignard compounds RO(CH$_2$)$_n$M(X) used in the process of the present invention may be made by reacting with magnesium the corresponding halide, RO(CH$_2$)$_n$X wherein 'R' is selected from a lower alkyl having 1 to 3 carbon atoms, 'n' is an integer from 3 to 6, and 'X' represents a halogen atom selected from Cl, Br or I. Preferably, the corresponding halide is a bromide. Typically, the reaction is carried out under dry nitrogen atmosphere, by reacting magnesium in a polar aprotic solvent with the corresponding halide, RO(CH$_2$)$_n$X added at such a rate that the reaction maintains a spontaneous gentle reflux until the end of its addition.

The process of the present invention is conducted in a polar aprotic solvent. Examples of polar aprotic solvents that may be used in the present invention include tetrahydrofuran, diisopropyl ether, diethyl ether, t-butylmethyl ether, 1,2-dimethoxy ethane and mixtures thereof. Preferably the solvent is selected from tetrahydrofuran, diisopropyl ether, diethyl ether, and t-butylmethyl ether. In more preferred embodiments of the present invention the polar aprotic solvent is tetrahydrofuran. The compounds may be reacted by adding a trifluoromethylbenzonitrile to an alkoxyalkyl Grignard or by adding an alkoxyalkyl Grignard to a trifluoromethylbenzonitrile, preferably by adding a trifluoromethylbenzonitrile to an alkoxyalkyl Grignard reagent. The addition may be carried out in the range of from about −40° C. to about reflux temperature of the solvent, and more preferably at temperature(s) in the range of from about 10° C. to about 20° C.

The addition of a trifluoromethylbenzonitrile to an alkoxyalkyl Grignard reagent may be carried out for a period of about 30 minutes to about 10 hours. In preferred embodiments of the present invention, the addition may be completed in about 30 minutes to about 2 hours.

After the addition, the reaction may be continued at the reflux temperature of the solvent for about 30 minutes to about 10 hours.

In preferred embodiments of the present invention the reaction may be complete in about 1 hour to about 4 hours. In more preferred embodiments of the present invention the reaction may be complete in about 1 hour to about 3 hours.

The reaction mixture is worked up by quenching into saturated ammonium chloride solution or by addition of hydrochloric acid solution. The organic layer is separated and the aqueous layer is further extracted with dichloromethane, the combined organic extract is dried over sodium sulfate, filtered and evaporated to dryness under vacuum to give the desired product, which may be purified by crystallization, distillation or by column chromatography.

The invention is illustrated but not restricted by the description in the following example.

EXAMPLE (4-Methoxybutyl)(4-trifluoromethylphenyl) methanone (II)

A dry three neck glass assembly, under dry nitrogen atmosphere, is charged with 150 g (6.17 moles) of magnesium and 2 L of anhydrous tetrahydrofuiran (THF). A small amount of iodine crystals or 1,2-dibromoethane is added to facilitate the initiation of Grignard reaction. The contents of the flask are heated to 75° C. and 975 g (5.84 moles) of 1-bromo-4-methoxybutane is added slowly at such a rate that the reaction maintains a spontaneous gentle reflux until the end of its addition. The Grignard reagent thus formed is cooled to 10 to 20° C. and a solution of 500 g (2.92 moles) of 4-trifluoromethylbenzonitrile in 2 L of tetrahydrofuran is introduced during a period of 1 hour to 2 hours while maintaining the reaction temperature at 16±2° C. by external cooling, if necessary. Thereafter the temperature is raised gradually to 60 to 70° C. over a period of 1 hour and further continued at that temperature until the reaction has gone to completion. The reaction mass is cooled, then quenched into ice cold hydrochloric acid and the THF layer is separated and concentrated. The aqueous layer is further extracted with dichloromethane which is added to the concentrate of the THF layer. The resulting dichloromethane solution washed with brine, dried over anhydrous sodium sulfate, and the solvent evaporated under reduced pressure to obtain a crude product, which is further purified by high vacuum distillation. The compound (4-methoxybutyl)(4-trifluoromethylphenyl)methanone (II) is obtained in 71.84% yield (546 g).

Analytical data: m.p 40–42° C.(purified by distillation).

$^1$H NMR: (CDCl$_3$, 200 MHz); (δ) 1.66–1.87 (m, —(CH$_2$)$_2$—,4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H).

$^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

The observed couplings due to fluorine ($^{19}$F) in the $^{13}$C NMR spectrum are in accordance with the literature reported values. (Spectral Data for Structural Determination of Organic Compounds, K. Biemann, Springer—Verlag, 1989, p. C245).

We claim:

1. A process for the preparation of (alkoxyalkyl)(4-trifluoromethylphenyl)methanones of formula 1:

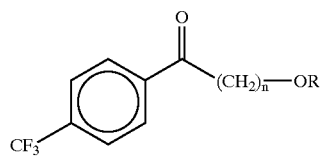

wherein R is selected from a lower alkyl having 1 to 3 carbon atoms and n is an integer from 3 to 6 comprising treating a 4-trifluoromethylbenzonitrilic (II) with an alkoxyalkyl Grignard reagent (IV),

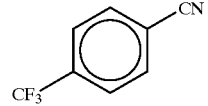

RO(CH$_2$)$_n$M(X)    IV wherein R is selected from a lower alkyl having 1 to 3 carbon atoms, n is an integer from 3 to 6, M is magnesium and X represents a halogen atom selected from Cl, Br or I.

2. A process according to claim 1 wherein the 'X' in RO(CH$_2$)$_n$M(X) is Br.

3. A process according to claim 1 wherein the compound of formula I is (4-methoxybutyl)(4-trifluoromethylphenyl) methanone.

4. A process according to claim 1, wherein the alkoxyalkyl Grignard RO(CH$_2$)$_n$M(X) is prepared from the corresponding RO(CH$_2$)$_n$X wherein 'R' is selected from a lower alkyl having 1 to 3 carbon atoms, 'n' is an integer from 3 to 6, 'M' is magnesium and 'X' represents a halogen atom selected from Cl, Br or I.

5. A process according to claim 4 wherein 'X' in RO(CH$_2$)$_n$X is Br.

6. A process according to claim 1 wherein 4-trifluoromethylbenzonitrile and alkoxyalkyl Grignard reagents are reacted together in a polar aprotic solvent.

7. A process according to claim 6 wherein the solvent is selected from the group consisting of tetrahydrofuran, diisopropylether, diethylether or mixtures thereof.

8. A process according to claim 1 wherein 4-trifluoromethylbenzonitrile and alkoxyalkyl Grignard reagents are reacted together at temperature(s) in the range from −40° C. to the reflux temperature of the solvent.

9. A process according to claim 8 wherein 4-trifluoromethylbenzonitrile and alkoxyalkyl Grignard reagents are reacted together at temperature(s) in the range from −40° C. to the reflux temperature of the solvent for a period of about 1 hour to 3 hours.

10. A process according to claim 1 wherein 4-trifluoromethylbenzonitrile and alkoxyalkyl Grignard reagents are reacted together at temperature(s) in the range from −40° C. to the reflux temperature of the solvent and thereafter the reaction is continued at the reflux temperature.

11. A process as claimed in claim 1 wherein the crude compound is crystallized or vacuum distilled to obtain pure compound of formula I as defined in claim 1.

12. (4-methoxybutyl)(4-trifluoromethylphenyl) methanone of formula 1 when prepared by the process according to claim 1.

13. (4-methoxybutyl)(4-trifluoromethylphenyl) methanone of formula 1 when prepared by the process according to claim 2.

14. (4-methoxybutyl)(4-trifluoromethylphenyl)methanone of formula 1 when prepared by the process according to claim 4.

15. (4-methoxybutyl)(4-trifluoromethylphenyl)methanone of formula 1 when prepared by the process according to claim 5.

16. (4-methoxybutyl)(4-trifluoromethylphenyl)methanone of formula 1 when prepared by the process according to claim 6.

17. (4-methoxybutyl)(4-trifluoromethylphenyl)methanone of formula 1 when prepared by the process according to claim 7.

18. (4-methoxybutyl)(4-trifluoromethylphenyl)methanone of formula 1 when prepared by the process according to claim 8.

19. (4-methoxybutyl)(4-fluoromethylphenyl)methanone of formula 1 when prepared by the process according to claim 9.

20. (4-methoxybutyl)(4-trifluoromethylphenyl)methanone of formula 1 when prepared by the process according to claim 10.

21. (4-methoxybutyl)(4-trifluoromethylphenyl)methanone of formula 1 when prepared by the process according to claim 11.

22. The process according to claim 1, wherein X is Br.

23. (4-methoxybutyl)(4-trifluoromethylphenyl)methanone of formula 1, when prepared by the process according to claim 1, having the following characteristics:
a melting point of about 40–42° C.;
$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and
$^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

24. (4-methoxybutyl)(4-trifluoromethylphenyl)methanone of formula 1, when prepared by the process according to claim 2, having the following characteristics:
a melting point of about 40–42° C.;
$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and
$^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

25. (4-methoxybutyl)(4-trifluoromethylphenyl)methanone of formula 1, when prepared by the process according to claim 4, having the following characteristics:
a melting point of about 40–42° C.;
$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and
$^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

26. (4-methoxybutyl)(4-trifluoromethylphenyl)methanone of formula 1, when prepared by the process according to claim 5, having the following characteristics:
a melting point of about 40–42° C.;
$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and
$^{13}$C NMR; (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

27. (4-methoxybutyl)(4-trifluoromethylphenyl)methanone of formula 1, when prepared by the process according to claim 6, having the following characteristics:
a melting point of about 40–42° C.;
$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and
$^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

28. (4-methoxybutyl)(4-trifluoromethylphenyl)methanone of formula 1, when prepared by the process according to claim 7, having the following characteristics:
melting point of about 40–42° C.,
$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and
$^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

29. (4-methoxybutyl)(4-trifluoromethylphenyl)methanone of formula 1, when prepared by the process according to claim 8, having the following characteristics:
a melting point of about 40–42° C.;
$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and
$^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

30. (4-methoxybutyl)(4-trifluoromethylphenyl)methanone of formula 1, when prepared by the process according to claim 9, having the following characteristics:

a melting point of about 40–42° C.;

$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and $^{13}$C NMR (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

31. (4-methoxybutyl)(4-trifluoromethylphenyl) methanone of formula 1, when prepared by the process according to claim 10, having the following characteristics:

a melting point of about 40–42° C.;

$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and $^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128,20 (d), 133.99(q; J=32.71 Hz (C—F coupling), aromatic quaternary carbon attached to —CF$_3$ group), 139.60 (s), 198.79 (s).

32. (4-methoxybutyl)(4-trifluoromethylphenyl) methanone of formula 1, when prepared by the process according to claim 11, having the following characteristics:

a melting point of about 40–42° C.;

$^1$H NMR: (CDCl$_3$, 200 MHz); (δ) 1.66–1.87 (m, —(CH$_2$)$_2$—, 4H); 3.04 (t, J=7.26 Hz, —(CH$_2$)—, 2H); 3.33 (s, —OCH$_3$, 3H); 3.43 (t, J=7.26 Hz, —(CH$_2$)—, 2H); 7.72 (d, J=8.30 Hz, 2H); 8.06 (d, J=8.30 Hz, 2H); and $^{13}$C NMR: (CDCl$_3$, 50 MHz); PPM 20.74 (t), 28.94 (t), 38.36 (t), 58.27 (q), 72.26(t), 123.53 (q, J=272.47 Hz (C—F coupling), —CF$_3$), 125.44 (d,q; J=3.51 Hz (C—F coupling), aromatic carbon ortho to —CF$_3$), 128.20 (d), 133.99(q; J=32.71 Hz (C—F coupling), aromatic quaternary carbon attached to —CF$_3$ group), 139.60 (s), 198.79 (s).

\* \* \* \* \*